United States Patent [19]

Aoki et al.

[11] 4,443,556
[45] Apr. 17, 1984

[54] CATALYST COMPOSITION

[75] Inventors: Kunitoshi Aoki, Kawasaki; Makoto Honda, Tokyo; Tetsuro Dozono, Yokosuka; Tsutomu Katsumata, Yokohama, all of Japan

[73] Assignee: Asahi Kasei Kogyo Kabushiki Kaisha, Tokyo, Japan

[21] Appl. No.: 429,054

[22] Filed: Sep. 30, 1982

[30] Foreign Application Priority Data

Oct. 20, 1981 [JP] Japan ............................. 56-166423

[51] Int. Cl.$^3$ .................. B01J 27/14; C07C 51/16; C07C 120/02
[52] U.S. Cl. ................................ 502/212; 562/546; 260/465.3
[58] Field of Search .............. 252/435, 437, 462, 470, 252/474

[56] References Cited

U.S. PATENT DOCUMENTS

| | | | |
|---|---|---|---|
| 3,712,912 | 1/1973 | Hausweiler et al. | 260/465.3 |
| 3,766,092 | 10/1973 | Honda et al. | 252/437 |
| 4,000,176 | 12/1976 | Umemura et al. | 260/465.3 |
| 4,001,317 | 1/1977 | Grasselli et al. | 260/533 N |
| 4,009,194 | 2/1977 | Umemura et al. | 260/465.3 |
| 4,036,870 | 7/1977 | Castellion | 260/465.3 |
| 4,070,390 | 1/1978 | Umemura et al. | 260/465.3 |
| 4,123,453 | 10/1978 | Grasselli et al. | 260/465.3 |
| 4,139,552 | 2/1979 | Grasselli et al. | 260/465.3 |
| 4,155,938 | 5/1979 | Yamamoto et al. | 252/462 X |
| 4,182,907 | 1/1980 | Grasselli et al. | 562/546 |
| 4,192,776 | 3/1980 | Grasselli et al. | 252/432 |
| 4,228,098 | 10/1980 | Aoki et al. | 260/465.3 |
| 4,290,922 | 9/1981 | Umemura et al. | 252/456 |
| 4,323,520 | 4/1982 | Hardman et al. | 260/465.9 |

FOREIGN PATENT DOCUMENTS

| | | |
|---|---|---|
| 47-16419 | 9/1972 | Japan . |
| 48-43096 | 4/1973 | Japan . |
| 48-49719 | 6/1973 | Japan . |
| 51-34107 | 3/1976 | Japan . |
| 5519227 | 7/1978 | Japan ......................... 252/437 |
| 54-95513 | 12/1979 | Japan . |
| 55-17334 | 7/1980 | Japan . |
| 55-17356 | 7/1980 | Japan . |
| 55-22639 | 8/1980 | Japan . |
| 1319190 | 6/1973 | United Kingdom . |
| 1347175 | 2/1974 | United Kingdom . |

OTHER PUBLICATIONS

Brunauer et al., "Adsorption of Gases on Multimolecular Layers", J. Am. Chem. Soc., 60, 309–319, (1938).

*Primary Examiner*—William G. Wright
*Attorney, Agent, or Firm*—Pennie & Edmonds

[57] ABSTRACT

A catalyst composition having a composition represented by the formula:

$$A_{0.1-4} B_{0.02-1} Mo_{12} Bi_{0.5-10} Fe_{0.5-10} Na_{0-3} P_{0-2} O_g$$

wherein A is at least one element selected from the group consisting of cerium, lanthanum, neodium, praseodium, samarium, europium and gadrinium, B is at least one element selected from the group consisting of potassium, rubidium and cesium, and g is the number of oxygen atoms required to satisfy the valence requirements of the other elements present, and supported on silica.

5 Claims, No Drawings

CATALYST COMPOSITION

DESCRIPTION

1. Technical Field

The present invention relates to a novel catalyst composition exhibiting excellent catalytic action on the production of acrolein, methacrolein, 1,3-butadiene, acrylonitrile or methacrylonitrile by the oxidation or ammoxidation of propylene, isobutylene, tert-butanol or 1-butene.

2. Background Art

It is known that there have been proposed a number of catalysts to be used for the production of acrolein, methacrolein, 1,3-butadiene, acrylonitrile or methacrylonitrile by the gaseous phase catalytic oxidation or ammoxidation of propylene, isobutylene, tert-butanol or 1-butene. For example, U.S. Pat. No. 3,766,092, U.K. Pat. No. 1,319,190 and U.S. Pat. No. 4,001,317 disclose multi-component oxide catalyst systems which contain molybdenum, bismuth and iron, and other ingredients such as cobalt, nickel, etc. as additives. Although subsequent improvements have been made on various aspects of catalyst systems of this type, when they are employed for the oxidation or ammoxidation of propylene, isobutylene, tert-butanol or 1-butene, the yield of the desired product drops within a short period of time. This adversely affects the suitability of such catalyst for industrial use.

In Japanese Laid-open Patent Application No. 95513/79 (U.S. Pat. No. 4,228,098), Japanese Laid-open Patent Application No. 17334/80, Japanese Laid-open Patent Application No. 17356/80 and Japanese Laid-open Patent Application No. 22639/80, some of the present inventors disclosed a catalyst comprising molybdenum, bismuth and iron and a small amount of at least one element selected from potassium, rubidium and cesium, which when employed for the oxidation or ammoxidation, gave a high yield and kept the yield for a long time.

The present inventors have made further extensive studies on the catalyst system and consequently found a catalyst additionally containing an element selected from cerium, lanthanum, neodymium, praseodymium, samarium, europium and gadolinium, which can be used for the oxidation or ammoxidation of propylene, tert-butanol or 1-butene to produce acrolein, methacrolein, 1,3-butadiene, acrylonitrile or methacrylonitrile, and gives a higher yield for a long time of the reaction. Moreover, it has also been found that above all in the ammoxidation, the production rate of acrylonitrile or methacrylonitrile can be improved to a great extent. The present invention has been accomplished based on these findings. The improvement in the production rate reduces the reactor size and the amount of the expensive catalyst and results in a great economical effect.

DISCLOSURE OF THE INVENTION

Accordingly, the primary object of the present invention is to provide an improved novel catalyst composition for producing acrolein, methacrolein, 1,3-butadiene, acrylonitrile or methacrylonitrile, at a higher yield and at a higher production rate by the oxidation or ammoxidation of propylene, isobutylene, tert-butanol or 1-butene.

More particularly the catalyst composition of this invention has a composition represented by the formula:

$$A_a B_b Mo_{12} Bi_c Fe_d Na_e P_f O_g$$

wherein

A is at least one element selected from the group consisting of cerium, lanthanum, neodymium, praseodymium, samarium, europium and gadolinium, B is at least one element selected from the group consisting of potassium, rubidium and cesium, a, b, c, d, e, f and g are the atomic ratios of A, B, molybdenum, bismuth, iron, sodium, phosphorus and oxygen, respectively, relative to twelve atoms of molybdenum, wherein:

a is between 0.1 and 4, b is between 0.02 and 1, c is between 0.5 and 10, d is between 0.5 and 10, e is between 0 and 3, f is between 0 and 2, and g is the number of oxygen atoms required to satisfy the valence requirements of the other elements present, and supported on silica.

In the catalyst composition of the present invention, the atomic ratio of the component A is $a=0.1-4$, preferably $a=0.3-3$. The component B is also essential, although minute in its amount, with an atomic ratio selected from the range of $b=0.02-1$, preferably $b=0.05-0.5$. The presence of sodium and phosphorus is not essential, but, when used in amounts within the range of the composition cited above, the abrasion resistance of the catalyst can be improved. As the carrier for the catalyst composition of the present invention, there may suitably be employed silica in an amount of 30 to 70% by weight, preferably 40 to 60% by weight, based on the total weight of the catalyst composition.

The catalyst composition of the present invention can be prepared according to the known method, for example, by first preparing a slurry of starting materials, then spray-drying the slurry and finally calcining the dried product. In the preparation of the slurry of the starting materials, as the sources for the respective catalyst components, there may suitably be employed silica gel for silica, phosphoric acid for phosphorus, ammonium salt for molybdenum and nitrates for other components, respectively. For this spray-drying of the starting material slurry, a centrifugal system may be preferably used. The calcination of the dried product may be conducted by carrying out a pre-calcination, if necessary, at 150° C. to 500° C., and then at a temperature in the range of from 600° C. to 750° C., preferably from 650° C. to 720° C., for 1 to 20 hours.

Production of acrolein, methacrolein, 1,3-butadiene, acrylonitrile or methacrylonitrile with the use of the catalyst composition of the present invention may be performed either in a fluidized bed reactor or in a fixed bed reactor. The reactant of propylene, isobutylene, tert-butanol, 1-butene or ammonia is not necessarily required to be of high purity, but of industrial grade. As the oxygen source, air is generally used.

EXAMPLES

A further understanding of the present invention, and the advantages thereof, can be had by reference to the following examples.

(1) Preparation of catalysts

According to the procedure described below, a catalyst composition was prepared having the formula:

$$Ce_{0.63}K_{0.075}Mo_{12}Bi_{2.42}Fe_{6.75}P_{0.3}O_g$$

supported on 50% by weight of silica.

To 166.7 g of a silica sol containing 30% by weight of SiO$_2$ [Snowtex-N, produced by Nissan Kagaku Co.] was added, with stirring, 0.59 g of 85% by weight of phosphoric acid, followed by a solution of 36.2 g of ammonium heptamolybdate [(NH$_4$)$_6$Mo$_7$O$_{24}$.4H$_2$O] dissolved in 90 g of water, and finally a mixed solution of 19.84 g of bismuth nitrate [Bi(NO$_3$)$_3$.5H$_2$O], 46.61 g of ferric nitrate [Fe(NO$_3$)$_3$.9H$_2$O], 4.70 g of cerium nitrate [Ce(NO$_3$)$_3$.6H$_2$O] and 0.1 g of potassium nitrate [KNO$_3$] previously dissolved in 33 g of 13.3% by weight nitric acid. The starting material slurry thus obtained was transferred into a co-current type spray-drier and dried at about 200° C. Spray-drying of the slurry was conducted by means of a spraying device equipped with a tray-type rotor arranged at the upper central portion of the drier. The resultant dried powders were transferred to a tunnel type kiln, precalcined at 400° C. for one hour and then calcined at 690° C. for 2 hours.

Using the foregoing procedure, the catalysts of the present invention and control catalysts were prepared, and their compositions are presented in Table 1 and Table 2. As the lanthanum, neodymium, praseodymium, samarium, europium, gadolinium, rubidium, cesium and sodium sources in the examples, the respective nitrates are employed. The calcination conditions were varied suitably as set forth in Table 1 and Table 2.

(2) Ammoxidation of propylene

The catalyst (1) as indicated in Table 1 (2 g) was charged into a Vycor glass reaction tube having an inner diameter of 8 mm, and a gas mixture of 6% by volume of propylene (volume ratio of propylene:ammonia:oxygen:nitrogen being 1:1.25:1.9:12.5) was passed through the tube at a flow rate of 2.1 liter/hour (calculated at NTP) at a temperature of 460° C. at atmospheric pressure. The result of this reaction was evaluated by the two indices of the acrylonitrile yield and the production rate of acrylonitrile as defined by the following formulas, and their values are shown in Table 1.

Acrylonitrile yield:

$$Y(\%) = \frac{\text{(Moles of acrylonitrile produced)}}{\text{(Moles of propylene fed)}} \times 100$$

Production rate of acrylonitrile: $R(Hr^{-1}) =$ $$\frac{\text{[Weight of acrylonitrile produced (g)]}}{\text{[Amount of catalyst used (g)]} \times \text{[Reaction time (Hr)]}} \times 100$$

The same reaction as above was repeated using each of the other catalysts listed in Table 1, and the results are also listed in Table 1. But, the flow rates of the gas mixtures were suitably varied as shown in Table 1.

(3) Ammoxidation of Isobutylene (or Tert-Butanol)

The catalyst (16) as indicated in Table 2 (1 g) was charged into a Vycor glass reaction tube having an inner diameter of 8 mm, and a gas mixture of 6% by volume of isobutylene (volume ratio of isobutylene:ammonia:oxygen:nitrogen being 1:1.5:2.5:11.7) was passed through the tube at a flow rate of 2.4 liter/hour (calculated at NTP) at a temperature of 460° C. at atmospheric pressure. The result of this reaction was evaluated by the two indices of the methacrylonitrile yield and the production rate of methacrylonitrile as defined by the following formulas, and their values are shown in Table 2.

Methacrylonitrile yield:

$$Y(\%) = \frac{\text{(Moles of methacrylonitrile produced)}}{\text{(Moles of isobutylene fed)}} \times 100$$

Production rate of methacrylonitrile: $R(Hr^{-1}) =$ $$\frac{\text{[Weight of methacrylonitrile produced (g)]}}{\text{[Amount of catalyst used (g)]} \times \text{[Reaction time (Hr)]}} \times 100$$

The same reaction as described above was repeated using each of the other catalysts listed in Table 2, and the results are also listed in the same Table 2. But, the flow rates of the gas mixtures were suitably varied as shown in Table 2. For the catalyst (16) and the control catalyst (22), the same ammoxidation as described above was repeated using tert-butanol in place of isobutylene to obtain the results as indicated in Table 2.

(4) Oxidation of Propylene

The catalyst (1) as indicated in Table 1 (1.5 g) was charged into a Vycor glass reaction tube having an inner diameter of 8 mm, and a gas mixture of 6% by volume of propylene (volume ratio of propylene:oxygen:steam:nitrogen being 1:1.9:3:10.8) was passed through the tube at a flow rate of 2.3 liter/hour (calculated at NTP) at a temperature of 380° C. at atmospheric pressure.

$$\text{Acrolein yield} = \frac{\text{(Moles of acrolein produced)}}{\text{(Moles of propylene fed)}} \times 100$$

was found to be 85.8%.

(5) Oxidation of Isobutylene

The catalyst (16) as indicated in Table 2 (1 g) was charged into a Vycor glass reaction tube of 8 mm inner diameter, and a gas mixture of 3% by volume of isobutylene (volume ratio of isobutylene:oxygen:steam:nitrogen being 1:2:3:27.3) was passed through the tube at a flow rate of 2.4 liter/hour (calculated at NTP) at a temperature of 400° C. at atmospheric pressure.

$$\text{Methacrolein yield} = \frac{\text{(Moles of methacrolein produced)}}{\text{(Moles of isobutylene fed)}} \times 100$$

was found to be 82.6%.

(6) Oxidation of 1-Butene

The catalyst (1) as indicated in Table 1 (1 g) was charged into a Vycor glass reaction tube having an inner diameter of 8 mm, and a gas mixture of 6% by volume of 1-butene (volume ratio of 1-butene:oxygen:steam:nitrogen being 1:1.8:3:10.9) was passed through the tube at a flow rate of 2.6 liter/hour (calculated at NTP) at a temperature of 370° C. at atmospheric pressure.

$$\text{1,3-Butadiene yeild} = \frac{\text{(Moles of 1,3-butadiene produced)}}{\text{(Moles of 1-butene fed)}} \times 100$$

was found to be 89.0%.

and oxygen, respectively, relative to twelve atoms of molybdenum, wherein:
a is between 0.1 and 4,
b is between 0.02 and 1,
c is between 0.5 and 10,

TABLE 1
Catalyst Composition and Results of Ammoxidation of Propylene

| | Cat. No. | A | B | Mo | Bi | Fe | Na | P | SiO$_2$ (wt %) | Calcination condition | Flow Rate (l/Hr at NTP) | Yield (%) | Production rate R(Hr$^{-1}$) |
|---|---|---|---|---|---|---|---|---|---|---|---|---|---|
| | 1 | Ce$_{0.63}$ | K$_{0.075}$ | 12 | 2.42 | 6.75 | 0 | 0.3 | 50 | 690° C., 6 Hr | 2.1 | 87.5 | 0.130 |
| | 2 | La$_{0.63}$ | " | " | " | " | " | " | " | 700° C., 4 Hr | 2.3 | 87.1 | 0.142 |
| | 3 | Nd$_{0.63}$ | " | " | " | " | " | " | " | 690° C., 2 Hr | 1.9 | 86.2 | 0.116 |
| | 4 | Pr$_{0.63}$ | " | " | " | " | " | " | " | " | " | 86.8 | 0.117 |
| | 5 | Sm$_{0.63}$ | " | " | " | " | " | " | " | " | 1.8 | 85.9 | 0.110 |
| Catalyst | 6 | Eu$_{0.63}$ | " | " | " | " | " | " | " | " | 2.0 | 86.3 | 0.123 |
| of the | 7 | Gd$_{0.63}$ | " | " | " | " | " | " | " | " | " | 86.0 | 0.122 |
| present | 8 | Ce$_{0.4}$La$_{0.23}$ | " | " | " | " | " | " | " | 700° C., 6 Hr | 2.3 | 87.2 | 0.142 |
| invention | 9 | Ce$_{0.63}$ | Rb$_{0.06}$ | " | " | " | " | " | " | 690° C., 4 Hr | 2.0 | 87.1 | 0.124 |
| | 10 | Ce$_{0.63}$ | K$_{0.03}$Cs$_{0.02}$ | " | " | " | " | " | " | " | " | 86.8 | 0.123 |
| | 11 | Ce$_{1.33}$ | K$_{0.075}$ | " | 3.67 | 5.00 | " | 0 | " | 690° C., 2 Hr | 1.9 | 86.7 | 0.117 |
| | 12 | Ce$_{2.10}$ | " | " | " | " | " | 1 | " | 710° C., 2 Hr | 1.8 | 85.8 | 0.109 |
| | 13 | Ce$_{0.80}$ | " | " | 2.80 | 4.40 | 1.2 | 0 | " | 700° C., 2 Hr | 1.9 | 86.2 | 0.116 |
| Control | 14 | — | " | " | 2.42 | 6.75 | 0 | 0.3 | " | 690° C., 2 Hr | 1.3 | 85.2 | 0.078 |
| catalyst | 15 | — | " | " | 4.07 | 7.15 | " | 1 | " | " | 1.2 | 85.4 | 0.073 |

TABLE 2
Catalyst Composition and Results of Ammoxidation of Isobutylene (or Tert-Butanol)

| | Cat. No. | A | B | Mo | Bi | Fe | Na | P | SiO$_2$ (wt %) | Calcination condition | Flow Rate (l/Hr at NTP) | Yield (%) | Production rate R(Hr$^{-1}$) |
|---|---|---|---|---|---|---|---|---|---|---|---|---|---|
| Catalyst | 16 | Ce$_{1.40}$ | K$_{0.3}$ | 12 | 2.77 | 4.47 | 0 | 1.2 | 50 | 690° C., 4 Hr | 2.4 | 82.1 | 0.354 |
| of the | | | | | | | | | | | 2.4* | 82.3 | 0.355 |
| present | 17 | La$_{1.0}$Sm$_{0.4}$ | " | " | " | " | " | " | " | " | 700° C., 2 Hr | 2.3 | 81.7 |
| invention | 18 | Eu$_{0.5}$Pr$_{0.9}$ | " | " | " | " | " | " | " | " | 690° C., 2 Hr | 2.2 | 80.5 | 0.318 |
| | 19 | Ce$_{0.8}$Gd$_{0.8}$ | " | " | " | " | " | 1.0 | " | " | 700° C., 2 Hr | " | 81.6 | 0.322 |
| | 20 | Ce$_{1.40}$ | K$_{0.2}$Rb$_{0.05}$ | " | " | " | " | 0 | " | " | 690° C., 2 Hr | 2.4 | 81.3 | 0.350 |
| | 21 | " | Cs$_{0.2}$ | " | " | " | " | " | " | " | " | 2.3 | 81.0 | 0.334 |
| Control | 22 | — | K$_{0.3}$ | " | " | " | " | " | " | " | " | 1.2 | 79.3 | 0.171 |
| catalyst | | | | | | | | | | | | 1.2** | 79.2 | 0.171 |
| | 23 | — | K$_{0.072}$ | " | 5.4 | 7.8 | " | " | " | " | 1.4 | 77.8 | 0.196 |

[Remark]
(*) and (**) are results of ammoxidation of tert-butanol, and others are those of isobutylene.

The foregoing examples illustrate, without limitation, the catalyst and process of the present invention. It is understood that changes and variations can be in the examples without departing from the spirit and scope of the invention as defined in the following claims.

Having thus described our invention, what we claim as new and desire to secure by Letters Patent is:

1. A catalyst composition having a composition represented by the formula:

$$A_aB_bMo_{12}Bi_cFe_dNa_ePfO_g$$

wherein
A is at least one element selected from the group consisting of cerium, lanthanum, neodymium, praseodymium, samarium, europium and gadolinium,
B is at least one element selected from the group consisting of potassium, rubidium and cesium,
a, b, c, d, e, f and g are the atomic ratios of A, B, molybdenum, bismuth, iron, sodium, phosphorus d is between 0.5 and 10,
e is between 0 and 3,
f is between 0 and 2, and
g is the number of oxygen atoms required to satisfy the valence requirements of the other elements present,
and supported on silica.

2. Catalyst composition of claim 1 wherein a is between 0.3 and 3.

3. Catalyst composition of claim 1 or 2 wherein b is between 0.05 and 0.5.

4. Catalyst composition of claim 1 wherein the silica is employed in an amount of 30 to 70% by weight based on total weight of the catalyst composition.

5. Catalyst composition of claim 4 wherein the silica is employed in an amount of 40 to 60% by weight based on total weight of the catalyst composition.

* * * * *

UNITED STATES PATENT AND TRADEMARK OFFICE
CERTIFICATE OF CORRECTION

PATENT NO. : 4,443,556
DATED : April 17, 1984
INVENTOR(S) : Kunitoshi Aoki, Makoto Honda, Tetsuro Dozono, Tsutomu Katsumata It is certified that error appears in the above-identified patent and that said Letters Patent are hereby corrected as shown below:

Column 2, line 45, "silica gel" should be -- silica sol--.

Columns 5-6, Table 2, line Cat. No. 17 (starting in "Calcination condition" column),
" " 700°C.,2Hr  2.3   81.7   "

should be
--700°C, 2Hr  2.3  81.7  0.377  --.

Signed and Sealed this

Seventeenth Day of July 1984

[SEAL]

Attest:

GERALD J. MOSSINGHOFF

Attesting Officer

Commissioner of Patents and Trademarks